(12) United States Patent
Feld et al.

(10) Patent No.: US 7,294,333 B1
(45) Date of Patent: Nov. 13, 2007

(54) NUCLEIC ACID CONSTRUCTS AND CELLS, AND METHODS UTILIZING SAME FOR MODIFYING THE ELECTROPHYSIOLOGICAL FUNCTION OF EXCITABLE TISSUES

(75) Inventors: Yair Feld, Haifa (IL); Lior Gepstein, Hafia (IL); Shimon Marom, Haifa (IL); Meira Frank, Haifa (IL)

(73) Assignee: GeneGrafts Ltd., Haifa (IL)

( * ) Notice: Subject to any disclaimer, the term of this patent is extended or adjusted under 35 U.S.C. 154(b) by 0 days.

(21) Appl. No.: 09/691,889

(22) Filed: Oct. 20, 2000

(51) Int. Cl.
*A01N 63/00* (2006.01)
*A01N 65/00* (2006.01)
*A61K 48/00* (2006.01)

(52) U.S. Cl. .................. 424/93.21; 424/93.1; 424/93.2

(58) Field of Classification Search ............... 424/93.1, 424/93.2, 93.21, 93.7; 514/44
See application file for complete search history.

(56) References Cited

U.S. PATENT DOCUMENTS

| | | | |
|---|---|---|---|
| 5,837,220 | A | 11/1998 | Blake et al. |
| 5,955,259 | A | 9/1999 | Holmes et al. |
| 6,013,766 | A | 1/2000 | Elgoyhen et al. |
| 6,087,488 | A | 7/2000 | Ganetzky et al. |
| 6,099,832 | A | 8/2000 | Mickle et al. |
| 6,100,046 | A | 8/2000 | Elgoyhen et al. |
| 6,110,459 | A | 8/2000 | Mickle et al. |
| 2004/0266717 | A1* | 12/2004 | Donahue et al. ............... 514/44 |

FOREIGN PATENT DOCUMENTS

| | | |
|---|---|---|
| WO | WO00/63434 | 10/2000 |
| WO | WO02/087419 | 11/2002 |

OTHER PUBLICATIONS

Crystal et al. Transfer of genes to humans: early lessons and obstacles to success pp. 404-410 1995.*
Deonarain Ligand-targeted receptor-mediated vectors for gene delivery pp. 53-69 1998.*
Friedmann Overcoming the Obstacles pp. 96-101 1997.*
Jackowski Neural injury repair: hope for the future as barriers to effective CNS regeneration become clearer pp. 303-317 1995.*
DeSilva Gene therapy's growing pains pp. 1050-1055 1995.*
Miller et al. Targeted vectors for gene therapy pp. 190-199 1995.*
Orkin et al. Report and recommendations of the panel to assess the NIH investment in research on gene therapy pp. 1-40 2002.*
Verma et al. Gene therapy-promises, problems and prospects pp. 239-242 1997.*
Koh et al. (1995) Stable fetal cardiomyocyte grafts in the hearts of dystrophic mice and dogs. J. Clin. Invest. 96: 2034-2042.*
Hoppe et al. (1999) Manipulation of cellular excitability by cell fusion: Effects of rapid introduction of transient outward K+ current on the guinea pig action potential. Circulation Research 84: 964-672.*
Donahue et al. (2005) Gene therapy for cardiac arrhythmias. Trends Cardiovasc. Med. 15(6): 219-224.*
Donahue et al. (2005) Modification of cellular communication by gene transfer. Ann. N.Y. Acad. Sci. 1047: 157-165.*
Meir et al. (1999) Ion channels in presynaptic nerve terminals and control of transmitter release. Physiological Reviews 79(3): 1019-1080.*
Rubanyi et al. (2001) The future of human gene therapy. Molecular Aspects of Medicine 22: 113-142.*
Tomaselli et al. (2003) Somatic gene transfer and cardiac arrhythmias: Problems and prospects. J. Cardiovasc. Electrophysiol. 14: 547-550.*
Feld et al. "Electrophysiological Modulation of Cardiomyocytic Tissue by Transfected Fibroblasts Expressing Potassium Channels: A Novel Strategy to Manipulate Excitability", Circulation 105(4): 522-9, 2002.
Hammond et al. "Angiogenic Gene Therapy for Heart Disease: A Review of Animal Studies and Clinical Trials", Cardiovasc Res 49(3): 561-7, 2001.
DeGroot et al. "Clinical Review 131: Gene Therapy for Thyroid Cancer: Where Do We Stand?", J Clin Endocrinol Metab 86(7): 2923-8, 2001.
Siegel "Biotechnology and Clinical Trials", J Infect Dis 185(Suppl 1): S52-7, 2002.
Reinlib et al. "Cell Transplantation as Future Therapy for Cardiovascular Disease?: A Workshop of the National Heart, Lung, and Blood Institute", Circulation 101(18): E182-7, 2000.
Roth et al. "Nonviral Transfer of the Gene Encoding Coagulation Factor VIII in Patients With Severe Hemophilia A", N Engl J Med 344(23): 1735-42, 2001.
Fast et al, "Anisotropic conduction in monolayers of neonatal rat heart cells cultured on collagen substrate", Circ Res. Sep. 1994;75(3):591-5.
Marshall "Gene Therapy's Growing Pains", Science 269: 1050-1055, 1995.
Verma et al. "Gene Therapy—Promises, Problems and Prospects", Nature 389(6648): 239-42, 1997.
Johns et al, "Adenovirus-mediated expression of a voltage-gated potassium channel in vitro (rat cardiac myocytes) and in vivo (rat liver). A novel strategy for modifying excitability", J Clin Invest. Aug. 1995;96(2):1152-8.
Nuss et al, "Overexpression of a human potassium channel suppresses cardiac hyperexcitability in rabbit ventricular myocytes", J Clin Invest. Mar. 1999;103(6):889-96.
Donahue et al, "Focal modification of electrical conduction in the heart by viral gene transfer", Nat Med. Dec. 2000;6(12):1395-8.
Miller et al. "Targeted Vectors for Gene Therapy", FASEB J. 9(2): 190-9, 1995.

(Continued)

*Primary Examiner*—Anne-Marie Falk

(57) ABSTRACT

A method of modifying the electrophysiological function of an excitable tissue region of an individual is provided. The method includes the step of implanting cells into the excitable tissue region. Each implanted cell is (a) capable of forming gap junctions with at least one cell of the excitable tissue region; and (b) capable of forming a functional ion channel or transporter, wherein the functional ion channel or transporter is capable of modifying the electrophysiological function of the excitable tissue region.

3 Claims, 8 Drawing Sheets

OTHER PUBLICATIONS

Orkin et al. "Report and Recommendations of the Panel to Assess the NIH Investment in Research on Gene Therapy": 1-40 1995, + http://.nih.gov/news/panelrep.html (1975).

Soonpaa et al. "Formation of Nascent Intercalated Disks Between Grafted Fetal Cardiomyocytes and Hot Myocardium", Science 264(5155): 98-101, 1994.

Rook et al, "Differences in gap junction channels between cardiac myocytes, fibroblasts, and heterologous pairs", Am J Physiol. Nov. 1992;263(5 Pt 1):C959-77.

Gussoni et al. "Normal Dystrophin Transcripts Detected in Duchenne Muscular Dystrophy Patients After Myoblast Transplantation", Nature 356(6368): 435-8, 1992.

Freed et al. "Survival of Implanted Fetal Dopamine Cells and Neurologic Improvement 12 to 46 Months After Transplantation for Parkinson's Disease", N Engl J Med 327(22): 1549-55, 1992.

Jockusch et al. "Long-Term Expression of Isomyosins and Myoendocrine Functions in Ectopic Grafts of Atrial Tissue", Proc Natl Acad Sci USA 83(19): 7325-9, 1986.

Bader et al. "Repair and Reorganization of Minced Cardiac Muscle in the Adult Newt (Notophthalmus Viridescens)", J Morphol 155(3): 349-57, 1978.

Lerche et al. "Ion Channels and Epilepsy", Am J Med Genet 106(2): 146-59, 2001.

Luo et al. "A Model of the Ventricular Cardiac Action Potential, Depolarization, Repolarization,and Their Interaction", Circ Res 68(6): 1501-26, 1991.

Marom et al. "Modeling State-Dependent Inactivation of Membrane Currents", Biophys J. 67(2): 515-20, 1994.

Marom "Slow Changes in the Availability of Voltage-Gated Ion Channels: Effects on the Dynamics of Excitable Membranes", J Membr Biol 161(2): 105-13, 1998.

Marom et al. "State-Dependent Inactivation of the Kv3 Potassium Channel", Biophysical Journal 67:579-589, 1994.

Crystal "Transfer of Genese to Humans: Early Lessons and Obstacles to Success", Science 270: 404-410, 1995.

Deonarain "Ligand-Targeted Receptor-Mediated Vectors for Gene Delivery", Exp. Opin. Ther. Patents 8(1): 53-69, 1988.

Friedmann "Overcoming the Obstacles to Gene Therapy", Sci Am 276(6): 96-101, 1997.

Jackowski "Neural Injury Repair: Hope for the Future as Barriers to Effective CNS Regeneration Become Clearer", British Journa of Neurosurgery 9(3): 303-17, 1995.

Sangro et al. "Gene Therapy of Neoplastic LiverDiseases", International Journal of Cell Biology, 35(2): 135-148, 2003. Abstract.

Bruckner "INGN-201. Introgen Therapeutics", Current Opinion Invetigating Drugs, 2(12): 1776-1785, 2001. Abstract.

Nasz et al. "Recombinant Adenovirus Vectors for Gene Therapy and Clinical Trials", Acta Microbiol.Immunol. Hung, 48(3-4): 323-348, 2001. Abstract.

Cohen et al. "ONYX-015-Onyx Pharmaceuticals", Current Opinion Investigating Drugs, 2(12): 1770-1775, 2001. Abstract.

Kirn "Oncolytic Virotherapy for Cancer with Adenovirus D11520 (Onyx-015): Results of Phase I and II Trials", Expert Opinion Biol. Ther., 1(3): 525-538, 2001. Abstract.

Merritt et al. "Clinical Evaluation of Adenoviral-Mediated P53 Gene Transfer: Review of INGN 201 Studies", Semin. Oncol., 28)Suppl. 16): 105-114, 2001. Abstract.

Banerjee "Genasense (Genta Inc)" Current Opinion Investig. Drugs, 2(4):574-580, 2001. Abstract.

Ebihara et al. "Co-Expression of Lens Fiber Connexins Modifies Hemi-Gap-Junctional Channel Behavior", Biophysical Journal, 76: 198-206, 1999.

Grosshans "Gene Therapy—When A Simple Concept Meets A Complex Reality. Review on Gene Therapy", Functional and Integrative Genomics, 1: 142-145, 2000.

Gage "Cell Therapy", Nature, 392(Suppl.): 18-24, 1998.

Race et al. "Muscle Regeneration of Injured Myocardium", Journal of Cellular Biochemistry, Suppl.150: 173, 1991. Abstract.

Race et al. "Satellite Cells for Myocardial Regeneration", Physiologost., 32: 220, 1989. Abstract.

Marelli et al. "Satellite Cell Implantation for Neo-Myocardial Regeneration", First International Congress of the Cell Transplanty Society, 1(2/3), 1992. Abstract.

Murry et al. "Skeletal Myoblast Transplantation for Repair of Myocardial Necrosis", Journal of Clinical Investment, 98(11): 2512-2533, 1996.

Chiu et al. "Cellular Cardiomyoplasty: Myocardial Regeneration With Satellite Cell Implantaion", Annual Meeting of the Thoraxic Surgeons, 60:12-18, 1995.

Koh et al. "Differentiation and Long-Term Survival of C2C12 Myoblast Grafts in Heart", Journal of Clinical Investigations, 92: 1549-1554, 1993.

Li et al. "Human Pediatric and Adult Ventricular Cardiomyocytes in Culture: Assessment of Phenotypic Changes With Passaging", Cardiovascular Research, 32: 362-373, 1996.

Li et al. "Cardiomyocyte Transplantation Improves Heart Function", Annual Meeting of Thoracic Surgeons, 62: 654-661, 1996.

Li et al. "Method of Culturing Cardiomyocytes From Human Pediatric Ventricular Myocardium", Journal of Tissue Culture Methods, 14: 92-100, 1992.

Thompson "Fetal Transplants Show Promise", Science, 257: 868-870, 1992.

Leor et al. "Transplantation of Fetal Myocardial Tissue Into the Infarcted Myocardium of Rat—A Potential Method for Repair of Infarcted Myocardium?", Cell Transplants, 94(9 Suppl.II): 332-336, 1996.

Li et al. "In Vivo Survival and Function of Transplanted Rat Cardiomyocytes", Circulation Research, 78(2): 283-288, 1996.

* cited by examiner

Fig 1a  Fig 1b 1 ms
Fig 1d
stimuli
5 sec
Fig 1e
stimulus
50 msec pair duration (msec)
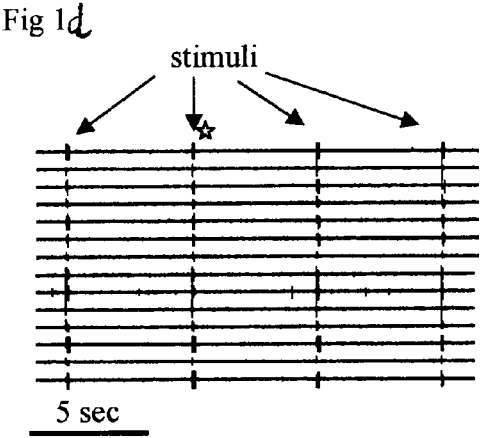
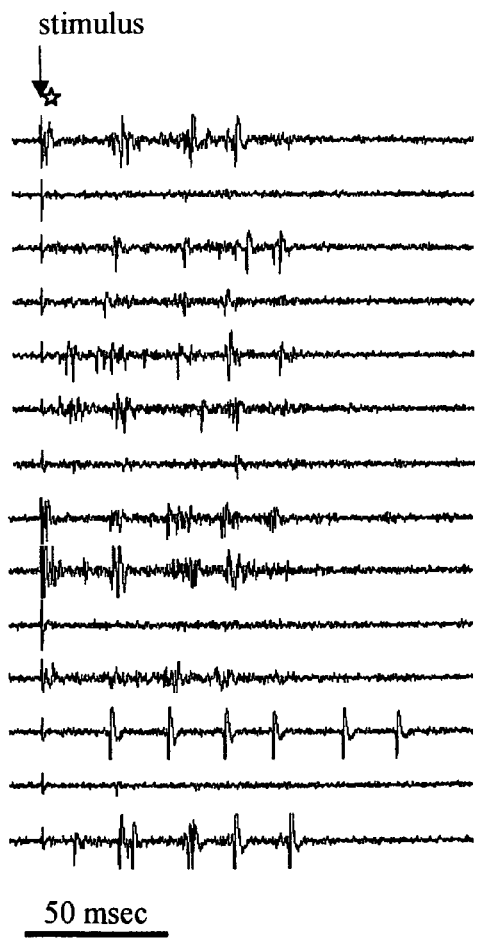

Fig 2a
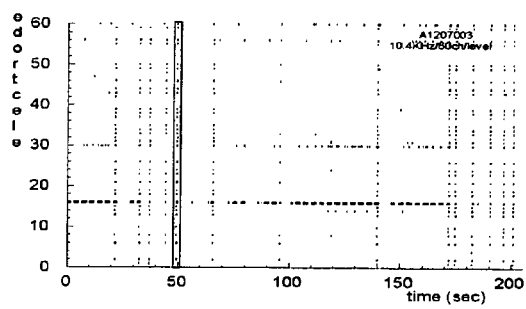
Fig 2b
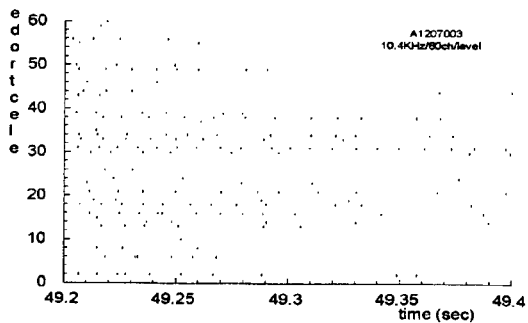
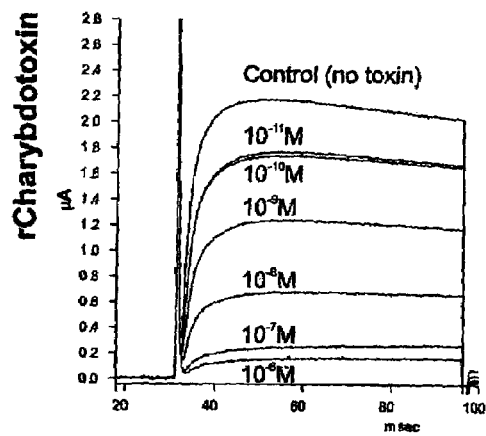
Fig. 3

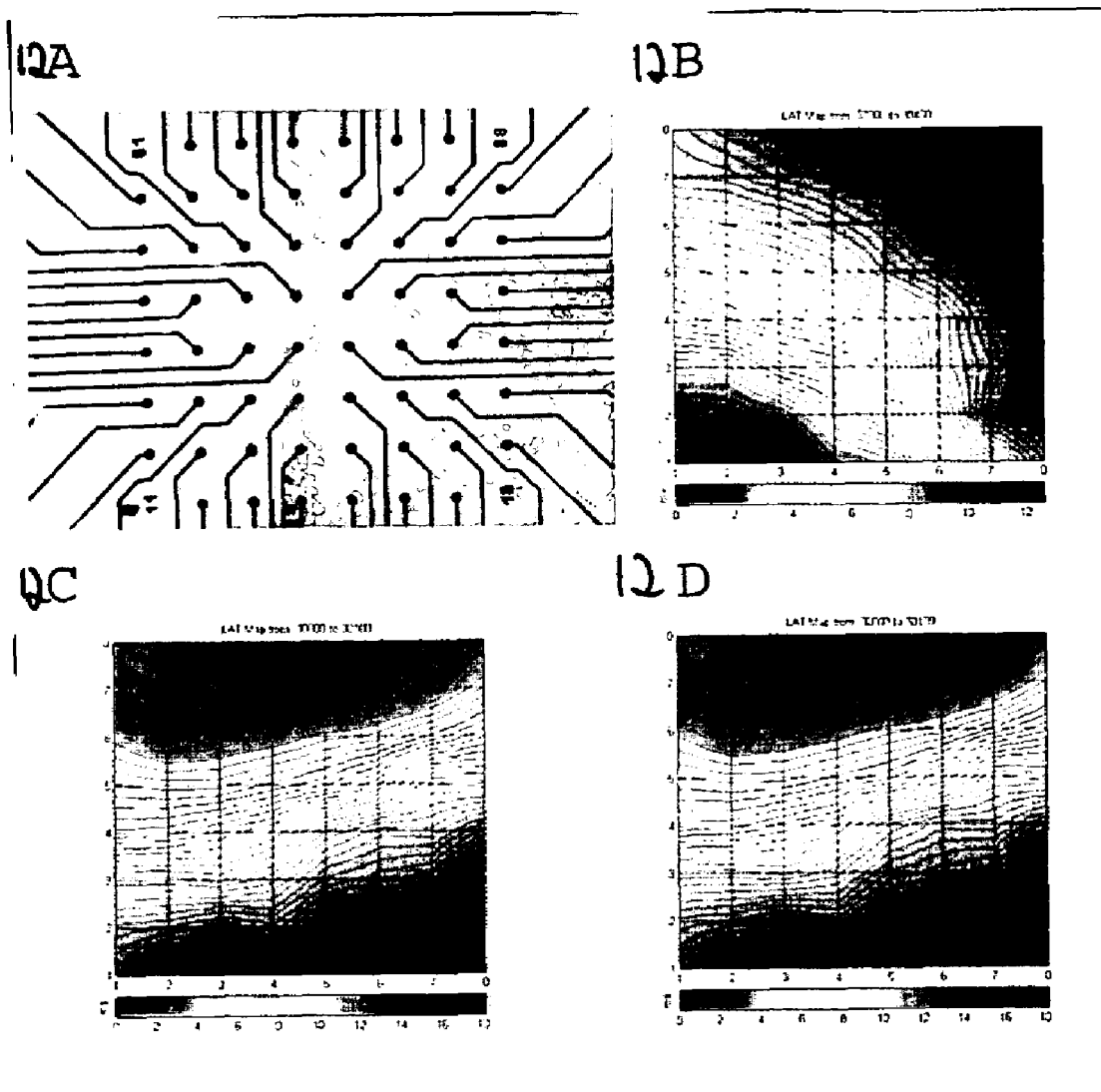
Figs. 12a-d

NUCLEIC ACID CONSTRUCTS AND CELLS, AND METHODS UTILIZING SAME FOR MODIFYING THE ELECTROPHYSIOLOGICAL FUNCTION OF EXCITABLE TISSUES

FIELD AND BACKGROUND OF THE INVENTION

The present invention relates to nucleic acid constructs and cells, and further to methods utilizing same for modifying the electrophysiological function of excitable tissues. More particularly, embodiments of the present invention relate to the use of cells having gap junctions and ion channels or transporters for modifying the electrophysiological function of excitable tissues.

The biological cell membrane, the interface between the cell and its environment, is a complex biochemical entity one of whose major involvement is the directed transport of specific substances. A related major involvement of the cell membrane is the maintenance of chemical gradients, particularly electrochemical gradients, across this interface. These gradients are of great functional significance (e.g., in the production of action potentials in nerve and muscle cells).

Ion channels are macromolecular protein pores, which span the cell membrane lipid bilayer. While approximately 30% of the energy expended in cells goes to maintain the ionic gradient across the cell membrane, it is the ion channel that dissipates this stored energy, much as a switch releases the electrical energy of a battery.

Ion channels are efficient compared to enzymes; small conformational changes gate a single channel between "closed" and "open" states, allowing up to $10^7$ ions to flow in one second, amounting to approximately $10^{-12}$ Amperes of highly selected ions flow during the channel opening. Since they are efficient, the number of ion channels per cell is relatively low; a few thousand channels of a given subtype/cell are usually sufficient to perform their task while orders of magnitude higher numbers of receptors or enzymes are required to carry out their tasks.

Ion channels are usually classified by the type of ion they selectively pass (sodium, potassium, calcium, or chloride) although some are indiscriminate. Different ion channels are activated (or gated) by either extracellular ligands, transmembrane voltage, or intracellular second messengers.

Ion Channel Conductance

Conductance quantifies the ease with which ions flow through a material and is expressed in units of charge/sec/volt. Single channel conductance, g, as distinguished from the membrane conductance (G) of the entire population of channels, is defined as the ratio of single channel current amplitude (i) to the electromotive force, or voltage (V):

$$g=i/V$$

The direction of ion movement through channels is governed by electrical and chemical concentration gradients. Entropy dictates that ions will flow passively through ion channels down a chemical gradient. Electrically charged ions will also move in an electrical field, just as ions in solution flow to one of the poles of a battery connected to the solution. The point at which the chemical driving force is just balanced by the electrical driving force is called the Nernst equilibrium (or reversal) potential. Above or below this point, a particular ion species will flow in the direction of the dominant force. The net electrical flow across a cell membrane is predictable given the concentrations of ions, the number, conductances, and selectivities of the channels, and their gating properties.

The modern method of deciphering ion channel function is by using patch clamp technology. In the patch clamp technique, a small polished electrode is pressed against the plasma membrane. For unknown reasons, the affinity between glass and cellular membrane is incredibly high; very few ions leak through this tight seal. In essence, the electrode isolates and captures all ions flowing through the 1-3 square microns of the cell membrane defined by the circular border of the glass pipette. The result is that the ionic current passing through a single ion channel can be collected and measured. The current through the attached patch (cell-attached), a detached patch (inside-out or outside-out), or the whole cell can be measured.

Ion Channel Building Blocks

Since ion channel function is easily measured in real time, most ion channels were cloned using the South African clawed toad (*Xenopus laevis*) oocyte. These oocytes are large enough to inject with exogenous mRNA and are capable of synthesizing the resulting foreign proteins. In expression cloning, in vitro transcripts (mRNA) from a cDNA library derived from a source of tissue/cell known to be rich in a particular current are injected into individual oocytes. The proteins encoded by this library are allowed several days to be translated and processed before the oocyte currents are measured by voltage clamp techniques. The cDNA library (with ~1 million unique clones) is serially subdivided until injected messenger RNA from a single cDNA clone is isolated that confers novel ion channel activity. Moreover, mutant cDNA clones with engineered alterations in the protein's primary structure can be expressed and the ion channel properties studied in order to determine regions of the protein critical for channel activation, inactivation, ion permeation, or drug interaction.

The building blocks for most channel proteins are individual polypeptide subunits or domains of subunits each containing six hydrophobic transmembrane regions labeled S1 through S6. The Na+ and Ca2+ channel pores are single (a) subunits in which 4 repeats of the six transmembrane spanning domain surround the pore. Voltage-gated K+ channels (Kv; nomenclature refers to K channel, voltage-dependent) are encoded by a tetramer of separate six-transmembrane spanning motifs. Coassembly of the linked domains form the central pore and confer the basic gating and permeation properties characteristic of the channel type. The peptide chain (H5 or P loop) juxtaposed between the membrane spanning segments S5 and S6 project into and line the water-filled channel pore. Mutations in this region alter the channel's permeation properties. S4 is probably the major channel voltage sensor since it contains a cluster of positively charged amino acids (lysines and arginines). Voltage-dependent channel inactivation is mediated by a tethered amino terminal blocking particle (called the ball and chain mechanism) which swings in to occlude the permeation pathway (inactivation). Amino acids in the S6 transmembrane segment participate in another inactivation pathway named C-type inactivation.

The most recently discovered family of channel proteins are the inward rectifier K+-selective channels (Kir; K channel, inward rectifier). These channels determine the resting membrane potential in most cells because they are open at rest. Kir channel topography is similar to the Kv channel class but the subunits lack the S1 to S4 segments present in Kv channels. The two transmembrane spanning domain surrounding the conserved H5 pore domain is deceptively simple; heteromultimeric channel formation, direct G protein gating, and interactions with other proteins by some Kir subtypes considerably increases the complex behavior of this channel class.

Ion Transporters:

Yet another class of molecules which participate in ion transport across cellular membranes are the ion transporters. Ion transporters are integral membrane proteins capable of pumping one ion out of the cell while pumping another ion into the cell.

In, for example, Na/K ion transporters, the Na+, K+ pump activity is the result of an integral membrane protein called the Na+, K+-ATPase. The Na+, K+-ATPase consists of a "catalytic" α-subunit of about 100,000 daltons and a glycoprotein β-subunit of about 50,000 daltons. When operating near its capacity for ion transport, the Na+, K+-ATPase transport three sodium ions out of the cell and transport two potassium ions into the cell for each ATP hydrolyzed. The cyclic phosphorylation and dephosphorylation of the protein causes it to alternate between two conformations, E1 and E2. In E1 the ion-binding sites of the protein have high affinity for Na+ and face the cytoplasm. In the E2 conformation the ion-binding sites favor the binding of K+ and face the extracellular fluid.

Examples of other ion transporters include the Na/Ca exchange system which participates in regulation of intracellular Ca+; the Na/H exchange system which function in concert with a Cl/HCO3 exchange system to regulate intracellular pH; and the Na—K—Cl exchange system which contributes to smooth muscle function and which is regulated by a number of vasoactive agents.

Excitable Tissues

Myocardium: Myocardial contraction depends on the opening and closing of a complex series of ion channels in myocardial cell membranes.

The most prominent of these channels are the K+ Ca++ and Na+ ion channels.

The number of K+ ions is greater inside a resting myocardial cell than outside. But the number of Na+ ions is greater outside. When a myocardial cell beats, sodium channels open allowing a rapid, transient in-rush of Na+ ions, then close within about two one-thousandth's (2/1000) of a second. This depolarizes the membrane with the positive ions moving in. Then there is then a slower, but prolonged (½ second), release of potassium to the outside of the cell which repolarizes the cell membrane.

Although myocardial contraction is more complex and involves other ions and channels, the end result of this depolarization-repolarization is that the contractile filaments in the cell engage, and the cell contracts.

Nerve cells: Signal propagation through neuronal cells is also governed by ion influx/outflux through nerve cell membranes. In nerve cells, Na+, Ca++ and K+ channels participate in the generation and propagation of a nerve signal.

Glandular tissue: Secretion of glandular factors, such as hormones is in some cases effected by the excitation of secreting cells or tissues. For example, in the pancreas, T-type calcium channels along with cell-to-cell gap junctions participate in secretion of insulin.

Since ion channels participate in numerous physiological processes, damage to cells and/or channels of excitable tissues can be a cause for numerous disorders.

For example, heart conditions, such as reentrant arrhythmia, are brought about by the damage or death of myocardial cells, which can no longer support normal electrophysiological function. Secretion of factors from glandular tissue, such as insulin is also effected by damage to excitable cells forming this tissue, while nerve cell changes, as for instance in disorders such as epilepsy severely effects nerve signal function.

The present invention provides a novel approach for modifying the electrophysiological property and thus the electrophysiological function of excitable tissues.

This novel approach, which according to one embodiment of the present invention utilizes cellular implants, can be utilized for restoring normal electrophysiological function to damaged tissues such as heart, nerve or glandular tissues.

SUMMARY OF THE INVENTION

According to one aspect of the present invention there is provided a nucleic acid construct comprising: (a) a first polynucleotide region encoding at least one first polypeptide capable of forming a functional ion channel or transporter when expressed within a cell; and (b) a second polynucleotide region encoding at least one second polypeptide capable of forming a functional gap junction when expressed within the cell.

According to further features in preferred embodiments of the invention described below, the nucleic acid construct further comprising at least one promoter being for directing the transcription of the first polynucleotide and the second polynucleotide.

According to still further features in the described preferred embodiments the at least one promoter is functional in mammalian cells.

According to still further features in the described preferred embodiments the at least one promoter is selected from the group consisting of a constitutive promoter, a tissue specific promoter, an inducible promoter and a developmentally regulated promoter.

According to still further features in the described preferred embodiments the first polynucleotide region and the second polynucleotide region are transcriptionally fused via an IRES sequence.

According to still further features in the described preferred embodiments the at least one first polypeptide and the at least one second polypeptide are translationally fused via at least one protease recognition site.

According to still further features in the described preferred embodiments the at least one promoter includes two promoters, a first promoter for directing the transcription of the first polynucleotide and a second promoter for directing the transcription of the second polynucleotide.

According to another aspect of the present invention there is provided a nucleic acid construct system comprising: (a) a first nucleic acid construct including a first polynucleotide region encoding at least one first polypeptide capable of forming a functional ion channel or transporter when expressed within a cell; and (b) a second nucleic acid construct including a second polynucleotide region encoding at least one second polypeptide capable of forming a functional gap junction when expressed within the cell.

According to still further features in the described preferred embodiments the first nucleic acid construct further includes a first promoter being for directing the transcription of the first polynucleotide and further wherein the second nucleic acid construct further includes a second promoter being for directing the transcription of the second polynucleotide.

According to still further features in the described preferred embodiments each of the first and the second promoters is functional in mammalian cells.

According to still further features in the described preferred embodiments each of first and the second promoters is independently selected from the group consisting of a constitutive promoter, a tissue specific promoter, an inducible promoter and a developmentally regulated promoter.

According to still further features in the described preferred embodiments there is provided a cell, cell culture or tissue explant transformed with the nucleic acid constructs described above.

According to still further features in the described preferred embodiments the cell is selected from the group consisting of a fibroblast, a myoblast, an astroglial cell and an endothelial cell.

According to still further features in the described preferred embodiments the tissue explant is an organ tissue explant.

According to still further features in the described preferred embodiments there is provided a pharmaceutical composition comprising, as an active ingredient, the nucleic acid constructs described above.

According to still further features in the described preferred embodiments the ion channel is selected from the group consisting of a sodium ion channel, a potassium ion channel, a calcium ion channel and a chloride ion channel.

According to still further features in the described preferred embodiments the at least one first polypeptide is selected from the group consisting of a K channel polypeptide, a Na channel polypeptide, a Ca channel polypeptide, a Cl channel polypeptide, a Na/K transporter polypeptide, a Na/Ca transporter polypeptide, a Na/H transporter polypeptide and a Cl/HCO3 transporter polypeptide.

According to still further features in the described preferred embodiments the at least one second polypeptide is selected from the group consisting of connexin43, connexin45 and connexin26.

According to still another aspect of the present invention there is provided a method of modifying the electrophysiological function of an excitable tissue region of an individual, the method comprising the step of implanting cells into the excitable tissue region, each implanted cell being: (a) capable of forming gap junctions with at least one cell of the excitable tissue region; and (b) capable of forming a functional ion channel or transporter; the functional ion channel or transporter being capable of modifying the electrophysiological function of the excitable tissue region.

According to still further features in the described preferred embodiments the ion channel is selected from the group consisting of a sodium ion channel, a potassium ion channel, a calcium ion channel and a chloride ion channel.

According to still further features in the described preferred embodiments each implanted cell is transfected, prior to, or following implantation, with an exogenous polynucleotide expressing at least one polypeptide capable of forming the functional ion channel or transporter.

According to still further features in the described preferred embodiments each implanted cell is transformed, prior to, or following implantation, with an exogenous polynucleotide expressing at least one polypeptide capable of forming the gap junctions.

According to still further features in the described preferred embodiments expression of the at least one polypeptide from the exogenous polynucleotide is regulatable by an endogenous or an exogenous factor.

According to still further features in the described preferred embodiments an ion permeability of the functional ion channels is regulatable by an endogenous or an exogenous factor.

According to still further features in the described preferred embodiments the method further comprising the step of regulating the permeability of the functional ion channels, or the activity of the transporter to thereby regulate the electrophysiological function of the excitable tissue region.

According to still further features in the described preferred embodiments the step of regulating the permeability is affected by providing the exogenous factor to the excitable tissue region.

According to still further features in the described preferred embodiments each implanted cell is capable of forming the functional ion channel or transporter following induction.

According to still further features in the described preferred embodiments the excitable tissue region forms a part of an organ selected from the group consisting of a heart, a pancreas, a kidney, a brain and a liver.

According to still further features in the described preferred embodiments the method is utilized for regulating cardiac arrhythmia.

According to still further features in the described preferred embodiments the method is utilized for regulating secretion of endogenous factors from an organ including the excitable tissue region of the individual.

According to still further features in the described preferred embodiments the method is utilized for regulating neuronal discharge.

According to an additional aspect of the present invention there is provided a method of modifying the electrophysiological function of an excitable tissue region of an individual, the method comprising the step of expressing an exogenous polypeptide in at least a portion of cells forming a part of, or being in contact with, the excitable tissue region, the exogenous polypeptide being capable of forming functional ion channels or transporters within the at least a portion of the cells to thereby modify the electrophysiological function of the excitable tissue region.

According to still further features in the described preferred embodiments the method further comprising the step of expressing a second exogenous polypeptide in the at least a portion of the cells, the second exogenous polypeptide being capable of forming functional pap junctions within the at least a portion of the cells.

The present invention successfully addresses the shortcomings of the presently known configurations by providing a novel approach for modifying the electrophysiological function of excitable tissues.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-e illustrate results from experiments performed on large random cortical networks cultured on substrate-embedded multi-electrode arrays (MEA). FIGS. 1a-b—an image illustrating four out of sixty electrodes and the somata of numerous neurons growing on the surface (1a) and a magnification of a region thereof (1b). In the magnified image (1b) the richness of the connective (axo-dendritic) network is evident. Scale bar: 30 µm. FIG. 1c—exemplifies an action potential recorded from one electrode. The two parallel lines represent ±8RMS units for this particular electrode. Network response to focal stimulation. FIGS. 1d-e illustrate a reverberating response of the network to focal stimuli. A typical stimulus pulse lasts 420 µSec, and its amplitude is 50 µA. The traces were recorded simultaneously from different electrodes. Note the reverberating response to a stimulus (enlarged in FIG. 1e) which lasts 100 milliseconds or more.

FIG. 2a illustrates epileptic activity recorded from MEA in a mature (3 weeks in vitro) cultured cortical network. The network is prepared and recorded from as explained in FIG. 1. The recorded spontaneously bursting synchronous activity throughout the network is a characteristic feature of epileptic-like activity in networks of neurons.

FIG. 2b illustrates an expanded time scale of the activity marked by the red box (left side) revealing a complex structure of a single burst.

FIG. 3 illustrates the dose response to charybdotoxin of the Kv1.3 potassium channel.

FIG. 6a is a fluorescent image of a cardiomyocytes co-cultured with fibroblasts transfected with Kv1.3 channel coding sequences and labeled with Fast DiO (MAE cluster seeding pattern). The blue dot marks electrode 28 and the red dot marks electrode 53.

FIGS. 6b-c represent a two second recording of synchronous extracellular activity prior to seeding of the fibroblasts described in FIG. 6a. FIG. 6b—recording from electrode 28; FIG. 6c—recording from electrode 53;

FIGS. 6d-e represent a two second recording of uncoupled extracellular activity following seeding of the fibroblasts described in FIG. 6a and prior to treatment with CTX. FIG. 6d—recording from electrode 28; FIG. 6e—recording from electrode 53;

FIGS. 6f-g represent a two second recording of extracellular activity following seeding of the fibroblasts described in FIG. 6a and treatment with CTX 100 nM which reverses uncoupling effect. FIG. 6f—recording from electrode 28; FIG. 6g—recording from electrode 53;

FIG. 7a is a fluorescent image of cardiomyocytes co-cultured with fibroblasts transfected with Kv1.3 channel coding sequences and labeled with Fast DiO on a MEA (cluster seeding pattern).

FIG. 7b illustrates an activation map constructed prior to seeding of the fibroblasts described in FIG. 7a.

FIG. 7c is an activation map constructed five days following seeding of the fibroblasts described in FIG. 7a and prior to treatment with CTX illustrating the appearance of a conduction block.

FIG. 7d is an activation map constructed five days following seeding of the fibroblasts described in FIG. 7a and following treatment with CTX 10 nM illustrating the reversal of the conduction block.

FIG. 12a is a fluorescent image of MEA cultured cardiomyocytes and fibroblasts labeled with Fast DiO (cluster seeding pattern).

FIG. 12b illustrates an activation map constructed prior to seeding of the fibroblasts described in FIG. 12a.

FIG. 12c illustrates an activation map constructed five days following seeding of the fibroblasts described in FIG. 12a and prior to treatment with CTX, no conduction block is apparent.

FIG. 12d illustrates an activation map constructed five days following seeding of the fibroblasts described in FIG. 12a and following treatment with CTX (10 nM); no appreciable change from the activation map of FIG. 12c is evident.

DESCRIPTION OF THE PREFERRED EMBODIMENTS

Figure 1C:
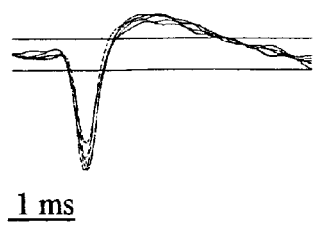
Figure 1F:
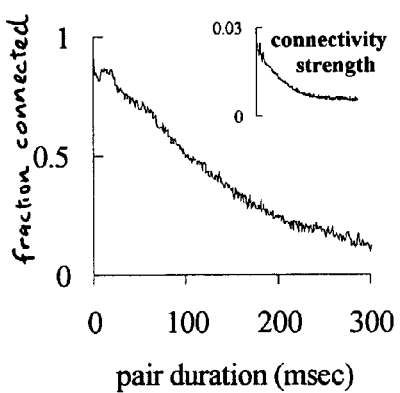
FIG. 1f is a graph illustrating the connectivity in cultured networks. The average number (four networks) of significantly occurring activity pairs formed between ten randomly chosen active (>0.2 Hz of spontaneous activity) electrodes. This number, normalized to the maximal number of possible activity pairs, is depicted as fraction connected, and shown to decrease as a function of within-pair time delay (ô). Inset: Given an A→B activity pair, the forecasting of B by A, which is the strength of the functional connectivity between the two, is given in terms of a correlation coefficient. This correlation is calculated from the number of times that the given pair appears within 1 hour, divided by the number of occurrences of A OR B. The average (n=4) functional connectivity strength as a function of 6 is shown.

The present invention is of nucleic acid constructs and cells, and of methods utilizing same for modifying the electrophysiological function of excitable tissues. Specifically, the present invention can be used to restore normal electrophysiological function to cells or tissues of, for example, damaged myocardium, neurons and secretory glands.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Since electrophysiological function of excitable tissues is governed by the quantity and type of ion channels present in the membrane of cells forming the excitable tissue, as well as the presence of gap junctions networking these cells, the present inventors propose that the electrophysiological function of any excitable tissue region can be modified by either expressing ion channel/transporter polypeptide(s) and/or gap junction polypeptide(s) within cells forming a part of, or being in contact with, the excitable tissue region or by implanting cells which posses ion channels/transporters and gap junctions within excitable tissues.

As used herein, the phrase "excitable tissue" refers to tissue which is composed, at least in part, of cells which respond to, or propagate, an electrochemical change. Examples include muscle tissue, neuronal tissue and glandular tissue.

According to the present invention, the introduction of new channels or channel producing cells into an excitable tissue, as well as the regulation of channel formation or permeability via endogenous or exogenous factors, can be utilized to control the electrophysiological function of excitable tissue to thereby treat various disorders associated with such tissues.

Thus, according to one aspect of the present invention, there is provided a nucleic acid construct including a first polynucleotide region encoding at least one first polypeptide which is capable of forming a functional ion channel or transporter when expressed within a cell, and a second polynucleotide region encoding at least one second polypeptide capable of forming a functional gap junction when expressed within the cell.

According to a preferred embodiment of the present invention, the first polynucleotide region encodes an ion channel forming polypeptide or polypeptides, such as, but not limited to, a Ca, K, Na or Cl ion channel forming polypeptide(s). For example, the first polynucleotide region can include the sequence set forth by nucleotides 179-6121 of Genbank Accession number AB027567, which when expressed within the cell produces a Na channel.

Additional examples of sequences which can be utilized by the present invention for forming a functional ion channel, when expressed within the cell, are listed according to their GenBank accession numbers in Tables 1-3 of the Example section which follows.

The first polynucleotide region can also encode any modified polypeptide (e.g. mutated, chimeric etc.) which is capable of forming functional ion channel in cells. Examples of mutated ion channel forming sequences are given in the Examples section which follows.

It will be appreciated that ion transporters such as Na/K, Na/Ca or Cl/HCO3 exchange systems (ATPases) can also be utilized by the present invention. Since such transporters are typically slower than channels in transporting ions across cell membranes, their use is limited to cases where rapid influx or outflux of ions is not required.

According to another preferred embodiment of the present invention, the gap junction forming polypeptide encoded by the second polynucleotide region is Connexin43 or 45, other connexin types which can be utilized by the present invention are described in the Examples section which follows.

The nucleic acid construct according to this aspect of the present invention also includes at least one promoter sequence for driving the transcription of the first and second polynucleotide regions. Preferably, the nucleic acid construct includes two promoters each driving transcription of a specific polynucleotide region. Alternatively, a single promoter sequence can transcribe both polynucleotide regions as a polycistronic message. Such a polycistronic message can include an internal ribosome entry site (IRES) between the first and second polynucleotide regions so as to enable the translation of the downstream polynucleotide region. Alternatively, the first and second polynucleotide regions of the polycistronic message can be translationally fused via a protease recognition site, such that a polypeptide translated from this message is cleaved into the first and second polypeptides described above.

It will be appreciated that although expressing both polynucleotide regions from a single construct is advantageous in some respects, each of the polynucleotide regions can alternatively be provided on a separate construct.

Thus, according to another aspect of the present invention there is provided a nucleic acid construct system which includes a first nucleic acid construct including a first polynucleotide region encoding at least one first polypeptide capable of forming a functional ion channel or transporter when expressed within a cell and a second nucleic acid construct including a second polynucleotide region encoding at least one second polypeptide capable of forming a functional gap junction when expressed within the cell.

The nucleic acid constructs of the present invention are utilized to transform cells, preferably mammalian cells, either in-vivo or ex-vivo.

As such the promoters utilized by these construct are mammalian functional promoters which are either constitutive, tissue specific, inducible or growth regulatable depending on the cell type and application.

The nucleic acid constructs described hereinabove are preferably constructed using commercially available mammalian expression vectors or derivatives thereof. Examples of suitable vectors include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives and modificants.

Any of the promoter and/or regulatory sequences included in the mammalian expression vectors described above can be utilized to direct the transcription of the polynucleotide regions described above. However, since such vectors are readily amenable to sequence modifications via standard recombinant techniques, additional regulatory elements, promoter and/or selection markers can easily be incorporated therein if needed.

The nucleic acid constructs of the present invention can be introduced into a cell, population of cells, or tissue via any standard in-vivo or ex-vivo mammalian transformation method. Such methods include, but are not limited to, direct DNA uptake techniques, and virus or liposome mediated transformation (for further detail see, for example, "Methods in Enzymology" Vol. 1-317, Academic Press).

The constructs according to the present invention can be administered to the individual per se, or in a pharmaceutical composition where it is mixed with suitable carriers or excipients.

Thus, according to another preferred embodiment of the present invention, the nucleic acid constructs according to the teachings of the present invention are included in a pharmaceutical composition which also includes a pharmaceutically acceptable carrier which serves for stabilizing and/or enhancing the accessibility or targeting of the constructs to target tissues.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect, i.e. the nucleic acid constructs of the present invention.

Hereinafter, the phrases "physiologically acceptable carrier" and "pharmaceutically acceptable carrier" are interchangeably used to refer to a carrier, such as, for example, a liposome, a virus, a micelle, or a protein, or a dilutent which do not cause significant irritation to an organism and do not abrogate the biological activity and properties of the active ingredient. An adjuvant is included under these phrases.

Herein the term "excipient" refers to an inert substance added to a pharmaceutical composition to further facilitate administration of an active ingredient. Examples, without limitation, of excipients, include calcium carbonate, calcium phosphate, various sugars and types of starch, cellulose derivatives, gelatin, vegetable oils and polyethylene glycols.

Techniques for formulation and administration of compositions may be found in "Remington's Pharmaceutical Sciences," Mack Publishing Co., Easton, Pa., latest edition, which is incorporated herein by reference.

Suitable routes of administration are preferably local rather than systemic, for example, via injection of the preparation directly into the excitable tissue region. For injection, the active ingredients of the invention may be formulated in aqueous solutions, preferably in physiologically compatible buffers such as Hank's solution, Ringer's solution, or physiological salt buffer.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically.

Pharmaceutical compositions suitable for use in context of the present invention include compositions wherein the active ingredients are contained in an amount effective to achieve the intended purpose.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer of the active ingredient. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed. (See e.g., Fingl, et al., 1975, in "The Pharmacological Basis of Therapeutics", Ch. 1 p. 1).

Direct administration of the nucleic acid constructs described hereinabove or of pharmaceutical compositions including such constructs into cells forming a part of, or being in contact with, the excitable tissue region is preferably used in cases where the cells of the excitable tissue to be transformed are viable and functional.

In cases where cell damage or death defines a disorder of excitable tissue, the preferred mode of treatment is implantation of transformed or non-transformed cells having ion channels/transporters and gap junctions.

Thus, according to another aspect of the present invention there is provided a method of modifying the electrophysiological function of an excitable tissue region of an individual. The method is effected by implanting cells into the excitable tissue region, wherein the implanted cells are each characterized by the ability to form gap junctions with at least one cell of the excitable tissue region and by the ability to form functional ion channels or transporters of one or more channel or transporter types.

Implantation of such cells can be effected by, for example, a syringe and needle adapted or fabricated for cell implantation, by a catheter drug delivery system (see for example, U.S. Pat. No. 6,102,887) or by standard neurosurgical methods.

As mentioned above, the implanted cells can be cells expressing endogenous ion channel and/or gap junction polypeptides, or modified cells transformed with the nucleic acid constructs of the present invention. Preferably, the implanted cells are mammalian cells, such as for example, muscle, or fibers cells (see the Examples section for further detail).

In any case, the cells and ion channel selectivity and gating-regulation types are selected according to the application. For example, in application where rapid channel gating is crucial, an ion channel of regulatable gating is selected. Gating Regulated channels, and factors utilizable for regulating gating are described in the examples section hereinbelow.

In addition, regulation of ion channel/transporter polypeptide expression through, for example, induced promoter activity or the like can also be effected as an alternative or additive regulatory mechanism for controlling ion influx or outflux.

Thus, the present invention provides a novel approach for modifying the electrophysiological function of excitable tissues. As is further detailed in the Examples section which follows, the present invention can be utilized to restore enhance or suppress electrophysiological function across a tissue region to thereby treat disorders caused by dysfunction in, or damage to, excitable tissues.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, cellular and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cardiac Applications

Cardiac arrhythmias are rhythm disturbances that result from alteration of the electrophysiological substrate of the heart. These arrhythmias include bradyarrhythmias (slow heart rate) which result from abnormalities in impulse formation or conduction and tachyarrhythmias (high heart rate) which result from abnormalities in the electrophysiological substrate and which lead to the formation of tachycardia via abnormal foci firing at high rate or via formation of reentry circuits.

Cardiac arrhythmia often results from damage to the electrophysiological tissue substrate of the heart. By transplanting cells transfected with various ionic channels of specific and predetermined properties, the methods of the present invention enable one to modify the electrophysiological properties of heart tissue and thus repair such arrhythmias. Thus, the present invention can be used to either increase excitability to treat bradyarrhythmias or modify the electrophysiological substrate in order to suppress or prevent tachyarrhythmias.

Numerous cell types can be utilized to accomplish such a task, provided the cells posses functional gap junctions and functional ion channels.

Examples of suitable cell types include, but are not limited to, fibroblasts, skeletal myoblasts (satellite cells), endothelial cells and the like which can be of autogenic, allogenic, or xenogenic origin.

The cells transplanted generate specific structural and function interactions with the cardiomyocytes via the gap junction which can be either inherent to the transplanted cells or the product of overexpressed exogenes (listed in Table 1 below).

TABLE 1

Sequences encoding polypeptide constituents of various ion channels

| Ion | Channel type | GenBank Accession numbers | Potential application |
|---|---|---|---|
| K | Kv1.3 | H18261 | Reentrant arrhythmia, Atrial fibrillation, Ventricular and atrial tachycardia or heart failure |
| K | inward rectifier potassium channel TWIK-1-human | S65566 | Atrial fibrillation or heart failure |
| K | Delayed rectifier potassium channel-human | L28168 L33815 M26685 | Atrial fibrilation or heart failure |
| K | Cardiac inward rectifier potassium channel-human | I38727 | Atrial fibrilation or heart failure |
| K | VOLTAGE-GATED POTASSIUM CHANNEL PROTEIN KV1.4 | M55514 AI631014 AI701825 AI694934 AI793138 | Atrial fibrilation or heart failure |
| K | 'voltage-gated potassium channel protein-human' | JC5275 | Atrial fibrilation or heart failure |
| K | OKCNQ2"; potassium channel | AF033348 | Atrial fibrilation or heart failure |
| K | 'inwardly rectifying potassium channel, hippocampal | I38521 | Reentrant arrhythmia, Atrial fibrillation, Ventricular and atrial tachycardia or heart failure |

TABLE 1-continued

Sequences encoding polypeptide constituents of various ion channels

| Ion | Channel type | GenBank Accession numbers | Potential application |
|---|---|---|---|
| K | VOLTAGE-GATED POTASSIUM CHANNEL PROTEIN KQT-LIKE 3.KCNQ3. | AF033347 AF071491 AW205596 AW135705 AA019129 AA001392 H86059 H08544 R36327 T78692 AI125802 H08545 R49258 | Atrial fibrilation or heart failure |
| Na | Sodium channel | AB027567 | A-V block, Atrial fibrillation, Sick sinus syndrome |
| Na | Voltage gated "SCN11A" | AF188679 | A-V block, Atrial fibrillation, Sick sinus syndrome |
| Na | 'AMILORIDE-SENSITIVE BRAIN SODIUM CHANNEL BNAC1' | U57352 U50352 H12215 Z45660 R35720 R15377 AA457638 AI473139 H12216 AI825456 R49357 T16341 F04549 R42118 | A-V block, Atrial fibrillation, Sick sinus syndrome |
| Na | hBNaC2"; product: "sodium channel 2 | U78181 AL035862 AA442069 AI017398 AI620655 AI762424 Z40887 AI700050 | A-V block, Atrial fibrillation, Sick sinus syndrome |
| Ca | T-type | AF134986 | Heart failure |
| Ca | 'VOLTAGE-DEPENDENT N-TYPE CALCIUM CHANNEL' | M94172 U76666 AA776162 T12610 | Heart failure |
| Ca | "L-type calcium channel (HFCC)"; Human' | M92269 AA927640 AA443875 AAI73146 | Heart failure |
| Ca | "CACNG4"; product: "calcium channel' | AF142625 | Heart failure |
| Ca | 'VOLTAGE-DEPENDENT L-TYPE CALCIUM CHANNEL,' | AJ224874 AJ006216 | Heart failure |
| Ca | "voltage-dependent calcium channel' | M92301 W07059 T28094 | Heart failure |
| Ca | L-type | M76558 AF055575 H29339 R25307 T27949 AA885750 AW029633 AI955764 AW008794 AA978315 AI914244 AI951788 AW008769 H29256 AI963788 AI537488 AA468565 AA523647 AI361691 R46658 AW139850 AI017959 AA701888 AA703120 AA877582 | Heart failure |
| Cl | 'probable chloride channel ClC-6-human' | S68428 | |
| Cl | "CLCN3"; product: "chloride channel protein' | AF029346 | |
| Cl | "ClC-2"; product: "chloride channel' | AF026004 | |
| Cl | "clc4"; product: "chloride channel" | AB019432 | |

The coupling between the transplanted and host cells forms a single functional unit. Such functional coupling of the transplanted cells with the myocytic tissue allows modification of the various action potential phases of the myocytes.

Listed below are some of the action potential modifications, which can be effected using the methods of the present invention.

(i) Transplantation of fibroblasts having potassium channels (KV1-3,É) can be utilized to reduce automaticity; the effect may be reversed by specific antagonist (e.g., Charybdotoxin)

(ii) Transplantation of fibroblasts having potassium channels (KV1-3,É) can also be utilized for the creation of block which can be reversed with CTX.

(iii) Transplantation of fibroblasts having sodium channels can be utilized for the creation of rate dependent conduction block. Na channels will be inactivated at fast (abnormal) rates but permit conduction at slower (physiological) rates.

(iv) Transplantation of cells having various channels (for example the human ether-a-go-go-related gene, HERG) can be used to repress abnormal focal activity (due to triggered activity and unstable repolarization).

(v) Transplantation of cells having KV channels can be utilized to regulate A-V node conduction (e.g., prolong refractoriness, or decrease conduction velocity).

(vi) Transplantation of cells having Na-channels or Na and K channels can be utilized to increase A-V node conduction.

(vii) Transplantation of cells having Na-channels can be utilized to increase excitability by increasing spontaneous rate and conduction within the SA node (pacemaker).

Transplantation Patterns:

The ability to transplant the cellular grafts of the present invention at predetermined myocardial sites may be of unique advantage since the location of the transplantation site can be selected and optimized according to the specific mechanism of the arrhythmia treated.

For example, a local effect may decrease side effects which result from a more generalized effect, as occurs for example, during pharmacological treatments.

A focal transplantation pattern may be used to treat focal arrhythmia or change excitability at predetermined sites. Linear lesion transplantation may be utilized to generate conduction blocks for the treatment of specific reentrant arrhythmia while diffuse transplantation patterns may be utilized to modify the excitable properties of entire regions.

Methods of Transplantation:

Several transplantation approaches can be utilized by the present invention. For example, an epicardial transplantation can be effected via surgical procedures, while an endocardial transplantation can be effected via catheters that are employed percutaneously and may be used to inject the cells endocardially. Alternatively, the cells may be injected into the coronary circulation.

Specific Applications:

Atrial fibrillation (AF): In atrial fibrillation, the normal rhythmical contractions of the cardiac atria are replaced by rapid irregular twitchings of the muscular wall; the ventricles respond in an irregular and rapid manner to the dysrhythmic bombardment from the atria. The pathological properties of AF can be modified using the teachings of the present invention via one of several possible approaches:

Cells transfected with specific ionic channel coding sequences, for example the voltage gated potassium channels (Kv1.3), can be transplanted into the A-V node. The modulating effect on the A-V node will slow the ventricular rate. This effect may be further modulated by dose-related changes resulting from the application of a blocking factor such as, for example, charybdotoxin.

The present invention also enables to treat AF by creating multiple line blocks (similar to the surgical maze procedure or the equivalent ablation procedure) in both atria. These blocks can be created by transplanting cells having K channels or rate dependent Na channels in the desired predetermined pattern.

The methods of the present invention cells may also be utilized to suppress pulmonary vein foci which often trigger AF, or to prevent their propagation to the atria by creating conduction blocks. By modifying the electrophysiological substrate of the atria the methods of the present invention can be used to increase cellular coupling and to increase and homogenize repolarization.

Atrial flutter and other Macroreentrant atrial arrhythmia: These arrhythmias result from macroreentrant wavefronts which can be treated by transplanting the cells to create a block at a critical area (for example the tricuspid-IVC isthmus in typical flutter).

Atrial tachycardia: Paroxysmal tachycardia originating in an ectopic focus in the atrium can be treated by cells transplanted at the area of the ectopic foci which suppress the abnormal activity.

Ventricular and reentrant tachycardia: The methods of the present invention can also be utilized to treat paroxysmal tachycardia originating in an ectopic focus in the ventricle by transplanting cells at the area of the ectopic foci. In addition, reentrant tachycardia originating from a scar tissue, following myocardial infarction is also treatable via the methods of the present invention. In this case, cellular grafts can be used to modify (increase or decrease) the conduction properties of slow conduction pathways within the scar which are critical for initiation and sustainment of the reentrant arrhythmia.

A-V block: An impairment of the normal conduction between atria and ventricles can be treated by cellular graft which improve the excitability properties of the A-V node thus reversing the conduction block.

Sick-sinus syndrome: An abnormal function of the SA node (normal pace maker) which results in a slow heart rate or alternating slow-fast rates can be treated by cells transplanted in the SA Node area in order to increase the excitability of the SA Node, or by creating an alternative pacemaker by transplanting cells with pace maker properties (combination of Na and K channels).

Heart failure: despite considerable advances in the diagnosis and treatment, congestive heart failure is the only major cardiovascular disorder which is increasing in incidence. Ventricular arrhythmias account for approximately 50% of the moralities associated with congestive heart failure. Ventricular arrhythmias typically arise from prolongation of the action potential duration (APD) which results in unstable repolarization and thus generation of arrhythmias. Treatment in these cases can be effected by shortening the action potential or by synchronizing repolarization. This can be achieved by transplanting cells having potassium channels (e.g. delayed rectifier or ether-go-go) which would function in shortening the cardiomyocytic APD.

Heart failure can also be treated by transplantation of cells having L-type or T-type calcium channels into the ventricles in a diffuse or a predetermined pattern in order to increase the excitability of the ventricles and to modulate calcium ion kinetics in the host myocardial tissue. Such transplantation would improve the contractility and relaxation pattern of the ventricles and thus change the systolic and diastolic properties of the ventricle.

Long OT syndrome: patients with genetic or acquired abnormalities in repolarization which display prolonged QT intervals may suffer from life-threatening malignant arrhythmias such as polymorphic VT. Such patients may be treated with the cellular grafts of the present invention having ion channels, such as potassium channels, which are selected capable of shortening and homogenizing repolarization.

Example 2

Pancreas

Diabetes Mellitus is a metabolic disease in which carbohydrate utilization is reduced while utilization of lipid and protein enhanced. Diabetes Mellitus is caused by relative deficiency of insulin, and is characterized, in more severe cases, by chronic hyperglycemia, glycosuria, water and electrolyte loss, and various organ damage causing significant morbidity and mortality.

Gap junctions and junction-mediated cell-to-cell communications are obligatory features of gland cells, regardless of their secretory products. Studies on pancreatic islets and acinar cells indicate that cell-to-cell communication via gap junction channels is required for proper biosynthesis, storage and release of both insulin and amylase. However, the endocrine and exocrine portions of the pancreas show opposite connexin (Cx) and coupling changes in relation to the activation and inhibition of their secretory functions. These differences may be accounted for by the expression of connexin43 (Cx43) in pancreatic islets and of Cx26 and Cx32 in pancreatic acini. This alternative expression of connexin isoforms is also found in several other endocrine and exocrine glands. These observations indicate that connexin-made channels play a central role in the control of secretory events (Meda, 1996, Clinical & Experimental Pharmacology & Physiology, December; 23(12):1053-7).

The function of T-type voltage-gated calcium channels in insulin-secreting cells has been previously described (Bhattacharjee et al, 1997 Endocrinology, Sep. 138(9):3735-40). Whole-cell voltage and current recordings, capacitance measurements, and RIA techniques were used to determine the contribution of T-type calcium channels in modulation of electrical activity and in stimulus-secretion coupling in a rat insulin secreting cell line, INS-1. Studies employing double pulse protocols in the current-clamp mode, uncovered that activation of T-type calcium channels provided a low threshold depolarizing potential that decreased the latency of onset of action potentials and increased the frequency of action potentials, both of which are abolished by administration of nickel chloride (NiCl$_2$), a selective T-type calcium channel blocker (Bhattacharjee et al, 1997 Endocrinology, Sep. 138 (9):3735-40).

Currently, treatment of non insulin dependent diabetes mellitus (NIDDM) includes, in more severe cases, drug therapy and insulin injections. The sulfonylureas family acts as ATP-sensitive potassium channels blockers, thus causing depolarization of the pancreatic b cells, calcium influx and insulin secretion.

Cellular grafts capable of forming gap junction (e.g. expressing Cx43) with pancreatic beta cells can be used by the present invention to treat NIDDM. These cells which can be of autogeneic, allogeneic or xenogeneic origin can be, for example, transfected ex-vivo with nucleic acid construct encoding a specific ion channel polypeptide(s), such as, for example, CACNA1G (encoded by GenBank Accession number AF134986) which forms a T-type voltage gated calcium channel (see Table 2 below for additional examples). The cells will be transplanted in the pancreas in a diffuse or a predetermined pattern via invasive or minimally invasive techniques. For example, minimally invasive percutaneous procedures using image guiding (CT, US etc.) can be used for transplantation of the cellular grafts.

Upon gap junction establishment, the cellular grafts will form a single compartment with the surrounding tissue and will increase the sensitivity of the pancreatic b cells to glucose levels by increasing the depolarization process and the sensitivity of insulin secretion to depolarization. For example, by using cells transfected with the T-type voltage gated calcium channels one may increase the ca influx following depolarization of the pancreatic cells thereby increasing insulin secretion.

Pharmacological blockage of these channels at a fine tuned dosage will prevent spontaneous action potentials thus preventing hypoglycemic states. This approach is advantageous since it allows to monitor insulin secretion regardless of the time of drug administration.

Several approaches can be utilized for regulating pancreatic beta cells excitability and insulin secretion. For example, transplantation of cells transfected with sodium or calcium channels can be utilized to increase depolarization of the beta cells or transplantation of cells transfected with calcium channels can be utilized to increase calcium influx thereby increasing beta cell sensitivity to depolarization. in addition these and other approaches can be utilized to increase and prolong the firing rate of such pancreatic cells.

TABLE 2

| Ion | Channel type | GenBank Accession numbers |
|---|---|---|
| Na | Sodium channel | AB027567 |
| Na | Voltage gated "SCN11A" | AFI88679 |

TABLE 2-continued

| Ion | Channel type | GenBank Accession numbers |
|---|---|---|
| Na | hBNaC2"; product: "sodium channel 2 | U78181 AL035862 AA442069 AI017398 AI620655 AI762424 Z40887 AI700050 |
| Ca | T-type | AF134986 |
| Ca | 'VOLTAGE-DEPENDENT N-TYPE CALCIUM CHANNEL' | M94172 U76666 AA776162 T12610 |
| Ca | "L-type calcium channel (HFCC)"; Human' | M92269 AA927640 AA443875 AA173146 |
| Ca | "CACNG4"; product: "calcium channel' | AF142625 |
| Ca | 'VOLTAGE-DEPENDENT L-TYPE CALCIUM CHANNEL,' | AJ224874 AJ006216 |
| Ca | "voltage-dependent calcium channel' | M92301 W07059 T28094 |
| Ca | L-type | M76558 AF055575 H29339 R25307 T27949 AA885750 AW029633 AI955764 AW008794 AA978315 AI914244 AI951788 AW008769 H29256 AI963788 AI537488 AA468565 AA523647 AI361691 R46658 AW139850 AI017959 AA701888 AA703120 AA877582 |

Example 3

CNS

Epilepsy:

Epilepsy is a chronic disorder usually associated with some alteration of consciousness and characterized by paroxysmal brain dysfunction due to excessive neuronal discharge.

Astroglial cells contribute to neuronal maintenance and function in the normal and diseased brain. Gap junctions, formed predominantly by connexin43 between astroglias, provide important pathways which coordinate astroglial responses (Reuss et al, 2000, Glia May; 30(3):231-41). Neuronal-glial interactions play an important role in information processing in the CNS. Previous studies have indicated that electro-tonic coupling between locus ceruleus (LC) neurons is involved in synchronizing the spontaneous activity. Moreover, Spontaneous oscillations in the membrane potential were observed in a subset of glial cells. These oscillations were synchronous with the firing of neurons, insensitive to transmitter receptor antagonists and disrupted by carbenoxolone, a gap junction blocker. Finally, immunoelectron microscopy studies established that connexins, the proteins that form gap junctions, were present on portions of the plasmalemma, bridging the cytoplasm of neurons and glia in LC (Alvarez et al, 2000, J. Neurosci. June 1; 20(11):4091-8).

Treatment of epilepsy can be effected by the present invention by transplantation of astroglial cells, fibroblasts or other cells transfected ex-vivo with a restraining force channel coding sequence exemplified in Table 3 below.

TABLE 3

| Ion | Channel type | GenBank Accession numbers |
|---|---|---|
| K | Kv1.3 | H18261 |
| K | inward rectifier potassium channel TWIK-1-human | S65566 |
| K | Delayed rectifier potassium channel-human | L28168 L33815 M26685 |

TABLE 3-continued

| Ion | Channel type | GenBank Accession numbers |
|---|---|---|
| K | Cardiac inward rectifier potassium channel-human | I38727 |
| K | VOLTAGE-GATED POTASSIUM CHANNEL PROTEIN KV1.4 | M55514 AI631014 AI701825 AI694934 AI793138 |
| K | 'voltage-gated potassium channel protein-human' | JC5275 |
| K | OKCNQ2"; potassium channel | AF033348 |
| K | 'inwardly rectifying potassium channel, hippocampal | I38521 |
| K | VOLTAGE-GATED POTASSIUM CHANNEL PROTEIN KQT-LIKE 3.KCNQ3. | AF033347 AF071491 AW205596 AW135705 AA019129 AA001392 H86059 H08544 R36327 T78692 AI125802 H08545 R49258 |

The transfected cells will be transplanted to the pathologic foci using standard neuro-surgical methods. Upon establishment of gap junction with the surrounding tissue, the cellular grafts form a single compartment which enables the repression of pathological tissue regions via controlled activation of the channels.

Example 4

Neuronal Networks

Neuronal cells were cultured on multi electrode arrays in efforts to determine electrophysiological function of these cultured cells under various conditions.

Culture Techniques:

Cortical neurons were obtained from newborn rats within 24 hours from birth, following standard harvesting procedures (Culturing nerve cells, $2^{nd}$ edition, Gary Ranker and Kimberly Goslin, 1998). The cortex tissue was digested enzymatically and mechanically dissociated and the neurons were plated directly onto substrate-integrated multi-electrode array (MEA) dishes prepared as described below. The cultures were bathed in MEM which was supplemented with heat-inactivated horse serum (5%), Glutamine (0.5 mM), Glucose (20 mM), and Gentamycin (10 µg/ml), and maintained in a tissue culture incubator at 37° C., 5% $CO_2$ and 95% during the recording phases. Half of the medium was exchanged twice a week and the experiments were performed during the third week following plating, thus allowing complete maturation of the neurons (FIGS. 1a-b).

It is a well known fact that electrical activity in a cultured neuronal network is dependent upon synaptic transmission. As shown by various published studies, this electrical activity can be blocked by perfusion with the N-Methyl-D-aspartate (NMDA), receptor antagonist D-2-amino-5-phosphonovalerate (APV), and non-NMDA receptor antagonist 6-cyano-7-nitroquinoxaline-2,3-dion (CNQX).

To determine the sensitivity and accuracy of the multi electrode array and detecting system of the present invention, prior art electrical activity studies in cultured neuronal networks were repeated as part of the present study using intracellular recordings as well as MEA recordings.

Electrophysiological Methods:

Arrays of 60 Ti/Au/TiN electrodes, 30 µm in diameter, spaced 200 µm from each other (MultiChannelSystems (MCS), Reutlingen, Germany) were utilized in the present study. The insulation layer (silicon nitride), was pretreated with poly-L-lysine forming a good surface for network development. A commercial 60-channel amplifier (B-MEA-1060, MCS, Reutlingen, Germany) with frequency limit range of 10-3000 Hz and a gain of ×1024 was utilized for signal amplification. The amplifier was connected to MCP-Plus filter amplifiers (Alpha Omega, Nazareth, Israel) for further amplification (×10 to ×20). Stimulation through the MEA was performed using a dedicated 8-channel stimulus generator (MCS, Reutlingen, Germany).

In addition, the micro-incubation environment was arranged to support long-term recordings from MEA dishes. This was achieved by streaming a filtered, heated and humidified air/$CO_2$ (95/5%) gas mixture, and by electrically heating the MEA platform to 37° C. Data is digitized using two 5200a/526 A/D boards (Microstar Laboratories, Wash., USA).

Experiments were first conducted in efforts to determine the functionality of the multi electrode array and the detecting system described above. The response of the cultured neuronal network to electrical stimuli is illustrated in FIGS. 1c-f.

Following electrical functionality determination, the neuronal network cultures were incubated with various electrical conduction blockers.

The addition of 5 µM bicuculin, 10 µM DNQX or 20 µM APV to the cultured neuronal network completely abolished spiking activity therein.

Epilepsy:

Epileptic activity of the cultured neuronal network described above was measured from the MEA described above. FIGS. 2a-b illustrate epileptic activity recorded from MEA in a mature (3 weeks in vitro) cultured cortical network. This recorded spontaneously bursting synchronous activity throughout the network is a characteristic feature of epileptic-like activity in networks of neurons.

Example 5

Although electrical coupling between fibroblasts and myocytes has been previously reported by Rook et al. (1992), the experiments conducted as a part of that study were designed in efforts to elucidate the validity of modulating excitable tissue by cellular graft. Thus, Rook et al. did not describe nor did they suggest the use of cells transfected with ion channel coding sequences for the purpose of modifying the electrophysiological function of excitable tissues.

While reducing the present invention to practice, the present inventors utilized a cell culture model system which included fibroblasts which were transfected with ion channel coding sequences and co-cultured with cardiomyocytes. These co-cultures enabled to test the effects of the ion channel expressing fibroblast on the electrophysiological function of the myocardial cells and to test the effects of various molecules which regulate channel permeability.

Materials and Methods

Preparation of Cultured Cardiomyocytes:

Monolayer cultures of neonatal rat ventricular cardiomyocytes (NRVM) were prepared as previously described (Rubin et al, 1995), with some modifications. The cultures were maintained in a humidified incubator under a controlled environment of 5% $CO_2$+95% air at 37° C.; fresh medium was replaced on alternating days.

Preparation of Fibroblast Cultures Transfected with Kv1.3:

Fibroblasts from the NIH 3T3 cell line were transfected with an expression cassette which included a mutant voltage gated potassium channel (Kv1.3) coding sequence (GeneBank Accession number H18261) placed under the transcription control of a constitutive promoter using standard procedures. Fibroblast cultures not transfected with the channel coding sequence were produced from the NIH 3T3 cell-line.

Figure 4A:
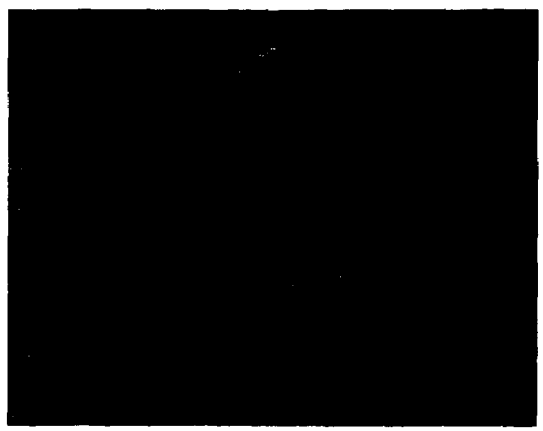
FIG. 4a illustrates a diffused fibroblast seeding pattern on multi electrode array (fibroblasts in red).
Figure 4B:
FIG. 4b illustrates a clustered fibroblast seeding pattern on multi electrode array.

Preparation of Co-Cultures:

Once well synchronous spontaneous activity was established in the cardiomyocyte cultures, fibroblasts transfected with the Kv1.3 channel coding sequence or non-transfected fibroblasts were added to the cultures. Two different methods where used to seed the fibroblasts. In the first method, the fibroblast were suspended in trypsin for 5 minutes following which they were seeded in a diffuse pattern in the cardiomyocytic cultures (FIG. 4a). In the second method, the fibroblasts where pipetted up and down through a 5 ml pipette for 2 minutes and seeded in the cardiomyocytic cultures thus were forming clusters of fibroblasts (FIG. 4b).

Immunohistochemistry:

The fibroblasts were labeled with Fast DiO [3,3'-dilinoleyloxacarbocyanine perchlorate (FAST DiO™ solid, Cat #-3898; Molecular Probes, USA) in order to track the fibroblasts in the co-cultures.

The Data Acquisition System and Electrical Activity Recording:

Extracellular recordings from cultured cardiomyocytes were performed on a PC-based Microelectrode Data Acquisition System (Multi Channel Systems, Reutlingen, Germany), consisting of Multi-Electrode Array (MEA), pre- and filter-amplifiers, data acquisition board, and software. The MEA consists of a 50×50 mm glass substrate, in the center of which is an embedded 0.7×0.7 or 1.4×1.4 mm matrix of 60 Titanium-nitride, gold contacts 10 or 30 µm diameter electrodes insulated with silicone nitride, with inter-electrode distance of 100 or 200 µm (there are no electrodes in the corners of the matrix). Data were recorded at 10-25 KHz with 12-bit precision. During the recording sessions, the MEA (removed from the regular incubator) was constantly perfused with a gas mixture consisting of 5% $CO_2$+95% air. Temperature was kept at 37±0.10° C.

Construction of Activation Maps:

Recorded data was filtered using cutoff frequency of 2 KHz (Fast et al, 1993). The filtered signal was then differentiated digitally to determine the Local Activation Time (LAT) at each electrode, corresponding to dF/dtmin (where F is the filtered signal) (Dolber and Spach, 1986). Color-coded activation maps were constructed by interpolating the LAT values for the sites between the electrodes, and by extrapolating the LAT values for the 4 corners of the MEA matrix. Activation maps were plotted by means of Matlab standard 2-d plotting function (pcolor) (Matlab 5.3 Mathworks Incorporated©). Conduction velocity was calculated by standard methods (Bayly et al, 1988).

Conduction Block:

Conduction block quantification is central to evaluating conduction block development in the cell cultures, and to evaluating reversibility of the conduction block following CTX application. A conduction block was determined using the following algorithm:

the local activation time (LAT) of each electrode was compared to the LAT of the four nearest electrodes, where $LATx$ is the local activation time at electrode x and $LATy$ is the local activation time at one of the four nearest electrodes to electrode x. Thus, If $LATx-LATy>0.25\times[LATmax$(last local activation time in the array)$-LATmin$(first local activation time in the array)], then the electrode was assigned a value of 1, else the electrode was assigned a value of 0. Each of the four electrodes was tested and if one or more satisfied this condition, then electrode x was set to a value −1, a sum of all the electrode values represented the block value.

Recording Protocol:

Electrical activity of the cultures was recorded on day one immediately prior to seeding of the fibroblasts and then daily until the cultures died or no spontaneous activity was detected. During the daily measurements the cultures where subjected to increasing concentrations (0.1, 1, 10, 100 nM) of CTX.

Results

Spontaneous Activity:

Measurement were performed during spontaneous activity from three groups of cardiomyocyte cultures: cultures without fibroblasts, cultures with NIH 3T3 fibroblasts (seeded diffusely) and cultures with transfected NIH 3T3 fibroblasts (expressing the mutant voltage gated potassium channel coding sequence).

Figure 5:
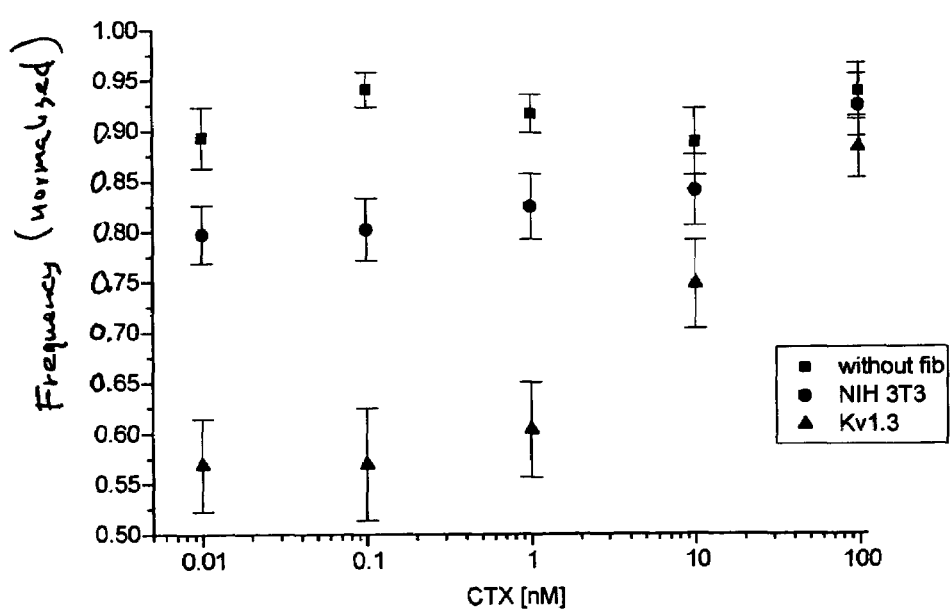
FIG. 5 illustrates the CTX frequency response of cultured cardiomyocytes (square), cardiomyocytes co-cultured with fibroblasts NIH 3T3 (dot) and cardiomyocytes co-cultured with fibroblasts (NIH 3T3) transfected with voltage gated potassium channel Kv1.3 coding sequence (triangle). c—no. of cultures; n—no. of measurements (without fibroblast—c=8; n=16, NIH 3T3—c=6; n=47, Kv1.3—c=6; n=43, error bar standard error).

The cultures where subjected to an increasing concentration of CTX from 0.1 to 100 nM. CTX caused a significant increase in the spontaneous activity rate in the co-cultures which included the transfected fibroblasts. The activity rate increased by 20 and 55% following administration of CTX concentrations of 10 and 100 nM respectively. In contrast, administration of CTX to cardiomyocyte cultures or to cardiomyocytes co-cultured with untransfected fibroblasts did not increase the activity rate at 10 nM and caused a modest increase of up to 15% at a 100 nM (FIG. 5).

There are three possible explanations for these results:

(i) Kv1.3 channel opening in transfected fibroblasts during action potential propagation causes hyperpolarization and therefore elongation of phase 4 at neighboring cardiomyocytes resulting in a slower activity rate; therefore, blocking of Kv1.3 channels with CTX reverses this effect.

(ii) CTX treatment increases electrical activity in areas that are blocked due to the presence of fibroblasts.

(iii) CTX enables propagation through otherwise blocked conduction tracts thus enabling propagation of action potentials. Since the area of the electrode array is a 1×1 $mm^2$ and since the area of the plate in which the array is embedded is about 2 $cm^2$, most of the culture activity is not recorded because propagation of electrical signal from cells positioned outside the array may be blocked prior to entering the array.

Application of CTX opens conduction blocks and thus enables activation of the myocytes at the electrode area.

The weak response observed in the control cultures treated with a high concentration of CTX is probably due to a minor blockage of potassium channels in the myocytes.

Figure 6:
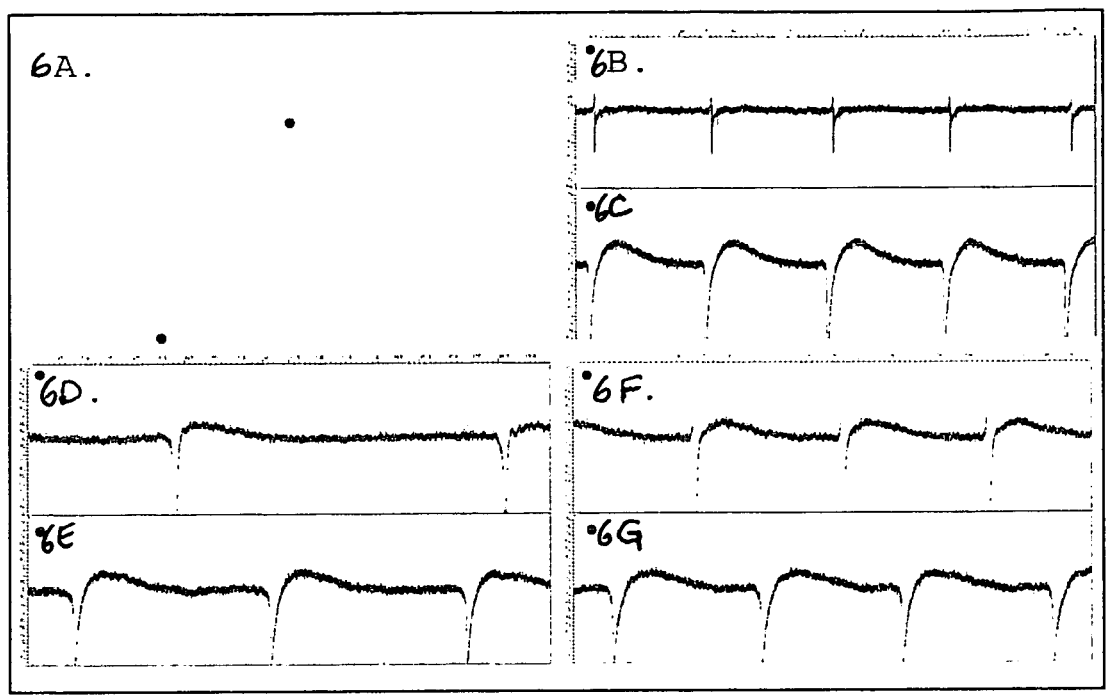
Figure 7:
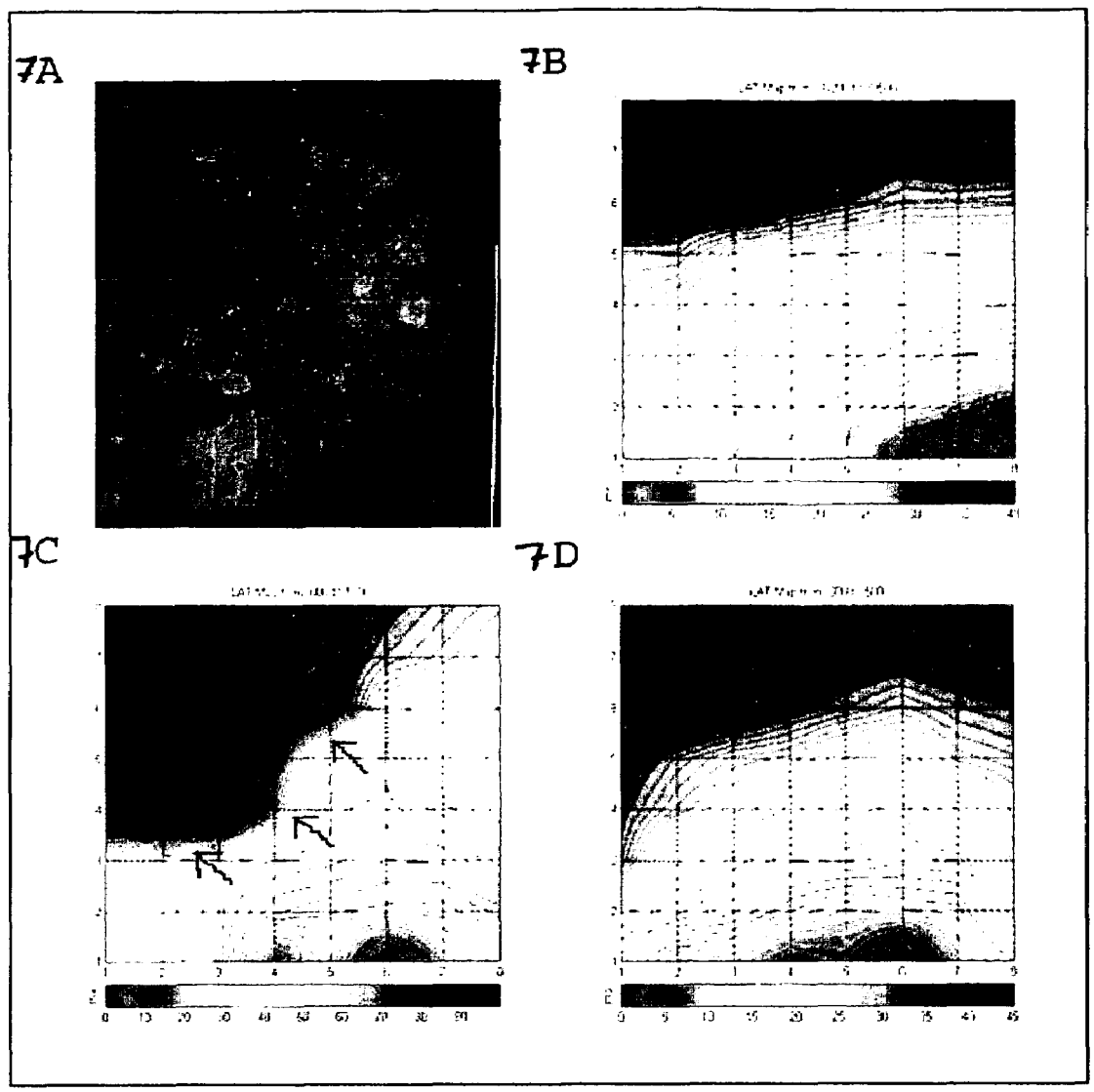
Figure 10:
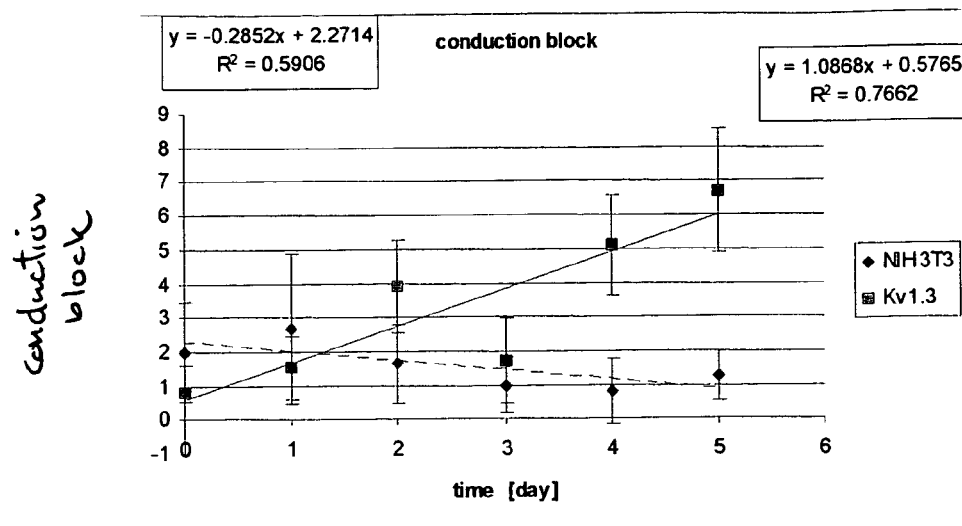
FIG. 10 illustrates the development of a conduction block in MEA seeded fibroblasts following measurement at day 0. A substantial increase in the conduction block factor was recorded from the culture including the fibroblast transfected with potassium channels (Kv1.3) (pink, n=5), while in the non-transfected fibroblast culture a decrease in the conduction block factor was recorded (blue, n=6).
Figure 11:
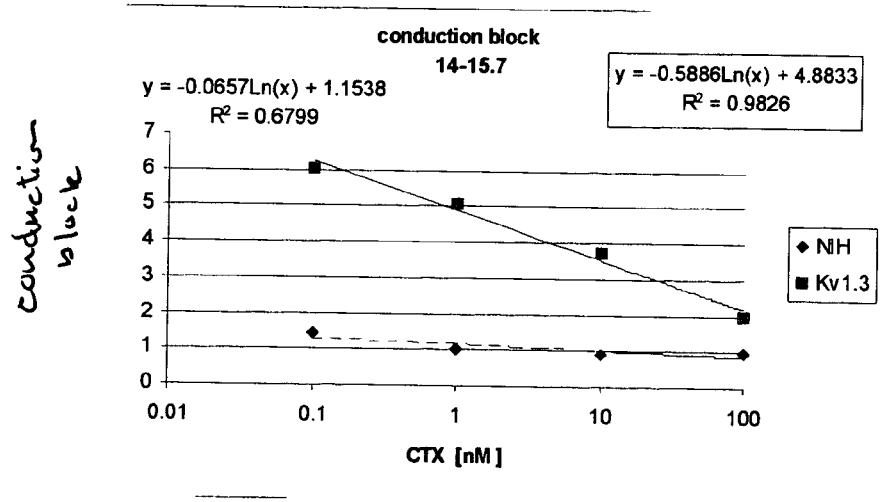
FIG. 11 illustrates the effects of Charybdotoxin (specific blocker of potassium channel Kv1.3) on conduction blocks. In co-cultures including fibroblasts transfected with Kv1.3, application of Charybdotoxin substantially decreased the conduction block factor (pink, n=10), while in co-cultures including non-transfected fibroblasts, a minimal response was recorded (blue, n=9).

Synchronous Activity and Conduction Block:

The two control culture types (with or without untransfected fibroblasts) exhibited a well-coupled synchronous activity throughout the experiment. Four of the co-cultures with transfected fibroblasts demonstrated an uncoupling effect following the fibroblasts seeding due to a conduction block generated by the Kv1.3 channels formed in the fibroblasts. Uncoupling effect was reversed following treatment with CTX (FIGS. 6f-g). Almost all of the cultures which included transfected fibroblasts demonstrated conduction blocks which developed following fibroblasts seeding (FIG. 10). Such conduction blocks were reversed following treatment with CTX (FIG. 7d and FIG. 11).

Figure 8:
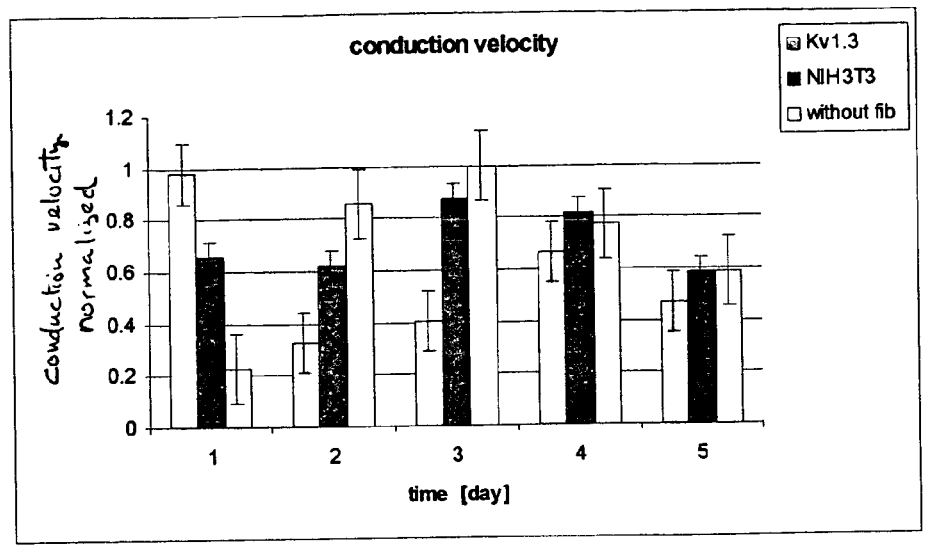
FIG. 8 illustrates the conduction velocity change throughout an experiment with seeded fibroblasts (in blue—myocytes with fibroblasts transfected with Kv1.3, in brown—myocytes with fibroblast without Transfection (control 1), in yellow—myocytes without fibroblast (control 2)); fibroblasts where seeded following measurements at day 1; Kv1.3 c=4, NIH 3T3 c=3, without fib c=1 error bar—standard error.

Cultures including non-transfected fibroblasts did not demonstrate conduction blocks or reversibility of blocks following application of CTX (FIGS. 12a-d). An immediate decrease in conduction velocity following transfected fibroblast seeding was also observed. Such an effect was not observed in co-cultures that included non-transfected fibroblasts (FIG. 8).

Figure 9:
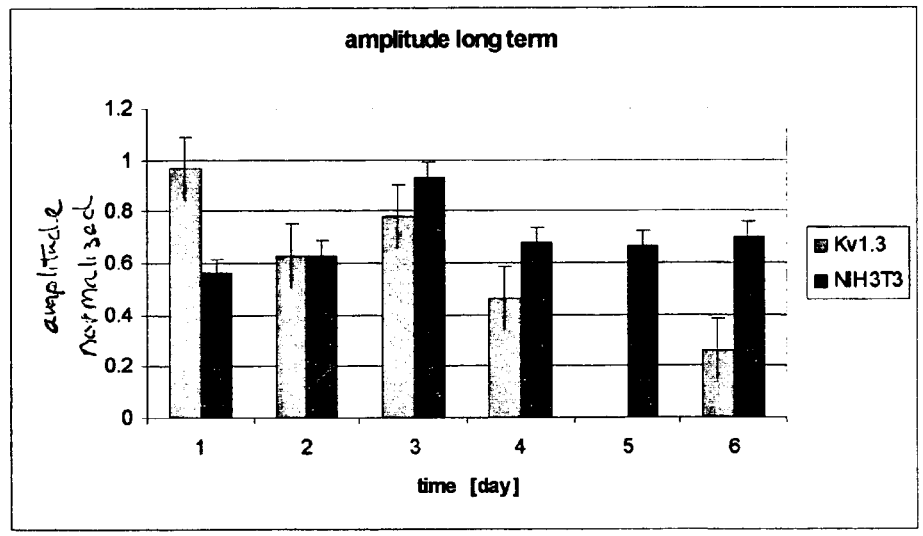
FIG. 9 illustrates the amplitude change throughout the experiment illustrated in FIG. 8; fibroblasts where seeded following measurements at day 1; Kv1.3 c=3, NIH 3T3 c=3 error bar—standard error.

Amplitude Change:

In comparison to cultures seeded with non-transfected fibroblasts, the amplitude of the extracellular signals decreased significantly following seeding with transfected fibroblasts (FIG. 9). This result may indicate a general decrease in culture excitability, implicating a reduced mass of action potential generating cardiomyocytes or the presence of slow conduction.

Summary and Future Directions

The above described results demonstrate for the first time that transplantation of fibroblasts transfected with a Kv1.3 channel coding sequence into cardiomyocytic cultures causes a significant change in the electrophysiological function of this excitable tissue.

Specifically, reduced spontaneous rate of the co-culture's excitability, lower amplitude of extracellular potentials, reduced conduction velocity and generations of local conduction blocks, were generated.

These changes where partially or fully reversed following administration of a specific Kv1.3 channel blocker, CTX. These results indicate the presence of tight structural and functional coupling between the fibroblasts and the myocytes, activation of the Kv1.3 channels and significant modulation of the electrical properties of the cultures.

Thus, the present invention provides a novel method which can be utilized to modulate the electrophysiological function of an excitable tissue region, which method can be utilized to treat various cardiac disorders.

The ability to modulate the electrophysiological properties of cardiac tissue may have significant clinical applications. Transplantation of cellular grafts having a predetermined electrical phenotype may be used, in the future, to alter the electrophysiological properties of cardiac tissue and together with pharmacological administration serve as a procedure for treating selected pathologies in the heart.

Furthermore, the method of the present invention is advantageous in that it effects a local tissue region rather then the heart as a whole, thus not affecting non-pathological tissue regions. This mode of treatment may be applied to treat a variety of cardiac arrhythmias.

For examples, transplantation of cellular grafts of the present invention to the AV node may be used for AV nodal modification, where the inherent properties of the cellular graft (the frequency response with or without specific pharmacology) can be used to modify the ventricular response during different atrial arrhythmias thus replacing the need for pharmacological treatment.

Local transplantation of the cellular grafts of the present invention may also be used to repress arrhythmogenic foci arising due to abnormal automaticity or to repress triggered activity by modulating the action potential in selected tissue regions.

In addition, reentrant arrhythmia may also benefit from the teachings of the present invention. Cellular grafts may be used to create a local conduction block in a critical area of the circuit thus treating the arrhythmia. Alternatively, predetermined seeding patterns may be used to create barriers or lines of conduction blocks for the treatment of more complex reentrant arrhythmias such as atrial fibrillation or flutter. In the later two cases, specific cell types can be used to allow normal conduction during slow (normal) rhythms, while creating local conduction blocks during fast (pathological) rhythms.

The teachings of the present invention may also be applied to modify the electrophysiological functionality of excitable tissues such as, for example, nervous tissue and glandular tissue. For examples, astrocyte transfected with selected ion channels may be used to modulate focal pathological areas in the CNS, thus enabling treatment of disorders such as epilepsy Parkinson and the like.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences disclosed therein and/or identified by a GeneBank accession number mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES

1. Bayly P. V, Bruce H. Ken Knight, Jack M. Rogers, Russel E. Hillsley, Raymond E. Ideker, William M. Smith. Estimation of conduction velocity vector fields from epicardial mapping data. IEEE transactions on biomedical engineering. 1988. 45:563-571.
2. Fast V G, Kleber A G. Microscopic conduction in cultured strands of neonatal rat heart cells measured with voltage-sensitive dyes. Circ Res. 1993. 73: 914-925.
3. Gussoni, E., Pavlath, G. K., Lanctot, A. M., Sharma, K. R., Miller, R G., Steinman, L. and Blau, H. M. Normal dystrophin transcripts detected in duchenne muscular dystrophy patients after myoblast transplantation. Nature. 1992.356:435-438.
4. Marom s, Goldstein S A, Kupper J, Levitan I B. Mechanism and modulation of inactivation of the Kv3 potassium channel. *Receptor and Channels*. 1993. 1:81-88.
5. Rook M B, Van Ginneken A C G, De Jonge B, Aoumari A E, Gros D, and Jongsma H J. Differences in gap junction channels between cardiac myocytes, fibroblasts, and heterologous pairs. Am J. Physiol. 1992. 263: C959-C977.
6. Rubin Y, Kessler-Icekson G, Navon G. The effect of furosemide on calcium ion concentration in myocardial cells. Cell Calcium. 1995 August; 18(2):135-9.
7. Spach M S, Dolber P C. Relating extracellular potentials and their derivatives to anisotropic propagation at a microscopic level in human cardiac muscle. Evidence for electrical uncoupling of side-to-side fiber connections with increasing age. Circ Res. 1986 March; 58(3):356-71.
8. Tompson, L. Fetal transplants show promise. Science. 1992. 257: 868-870.

What is claimed is:

1. A method of modifying the electrophysiological function of a heart of an individual and treating atrial fibrillation or ventricular tachycardia, the method comprising:

(a) providing allogeneic or autogeneic fibroblasts expressing an exogenous voltage-gated or inward-rectifier potassium ion channel polypeptide forming a functional ion channel; and
(b) implanting said allogeneic or autogeneic fibroblasts into the heart of the individual, such that each implanted cell of said allogeneic or autogeneic fibroblast forms:
   (i) gap junctions with at least one cell of the heart; and
   (ii) a functional ion channel;

thereby modifying the electrophysiological function of the heart and treating atrial fibrillation or ventricular tachycardia.

2. The method of claim 1, wherein each implanted cell of said allogeneic or autogeneic fibroblasts forms said functional ion channel following induction.

3. The method of claim 1, wherein said voltage-gated or inward-rectifier potassium ion channel is Kv1.3 or Kir2.1.

* * * * *